United States Patent [19]

Ruminski

[11] Patent Number: 5,602,155
[45] Date of Patent: Feb. 11, 1997

[54] PLATELET AGGREGATION INHIBITORS

[75] Inventor: Peter G. Ruminski, Ballwin, Mo.

[73] Assignee: G. D. Searle & Co., Chicago, Ill.

[21] Appl. No.: 375,338

[22] Filed: Jan. 17, 1995

[51] Int. Cl.$^6$ .................. C07D 213/36; C07D 213/56; C07D 213/57; A61K 31/44

[52] U.S. Cl. .................. 514/357; 546/279.1; 546/329; 546/330

[58] Field of Search .................. 546/329, 330; 514/357

[56] References Cited

U.S. PATENT DOCUMENTS

| | | | |
|---|---|---|---|
| 4,879,313 | 11/1989 | Tjoeng et al. | 514/564 |
| 4,952,562 | 8/1990 | Klein et al. | 514/530 |

FOREIGN PATENT DOCUMENTS

| | | |
|---|---|---|
| 0319506 | 6/1989 | European Pat. Off. . |
| WO91/04746 | 4/1991 | WIPO . |
| WO92/13552 | 8/1992 | WIPO . |
| WO92/17196 | 10/1992 | WIPO . |
| WO93/09795 | 5/1993 | WIPO . |

OTHER PUBLICATIONS

Fok et al. "Aminopeptidase resistant Arg–Gly–Asp analogs are stable in plasma and inhibit platelet aggregation." *Int. J. Peptide Protein Res.*, 38, 124–130 (1991).

Greenspoon et al. "Structural Analysis of Integrin–Mediated Cell Functions by Novel Nonpeptide Surrogates of the Arg–Gly–Asp Sequence." *Biochemistry*, 32, 1001–1008 (1993).

McDowell et al. "From Peptide to Non-Peptide. The Elucidation of a Bioactive Conformation of the Arg–Gly–Asp Acid Recognition Sequence." *J. Am. Chem. Soc.*, 116, 5069–5076 (1994).

*Primary Examiner*—Alan L. Rotman
*Attorney, Agent, or Firm*—Cynthia S. Kovacevic; Roger A. Williams

[57] ABSTRACT

This invention herein relates to compounds having the following formula

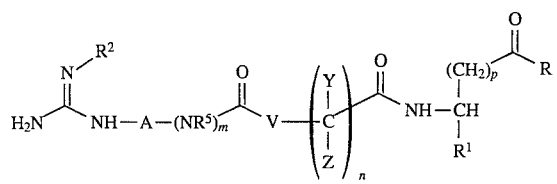

or a pharmaceutically acceptable salt thereof which are useful in the inhibition of platelet aggregation, to pharmaceutical compositions containing the compound and to a method of inhibiting platelet aggregation in mammals by administering such compounds and compositions.

7 Claims, No Drawings

PLATELET AGGREGATION INHIBITORS

FIELD OF THE INVENTION

The present invention relates to pharmaceutical agents (compounds) which inhibit platelet aggregation in mammals.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as GP IIb/IIIa; this is an important feature of the platelet function. Inhibitors of this interaction are useful in modulating platelet thrombus formation.

It is also known that another large glycoprotein named fibronectin, which is a major extracellular matrix protein, interacts with platelets. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., Ibid. 83, 5708–5712 (1986); Ginsberg et al., *J. Biol. Chem.* 260 (7), 3931–3936 (1985); Haverstick et al., *Blood* 66 (4), 946–952 (1985); and Ruoslahti and Pierschbacher, *Science* 238, 491–497 (1987). Still other such inhibitory peptides are disclosed in European Patent Applications 275,748 and 298,820.

U.S. Pat. No. 4,899,313 discloses peptide mimetic compounds containing a guanidino group which are useful as platelet aggregation inhibitors.

European Patent Application 512,831 discloses piperidinylalkylazacycloalkanones which inhibit the binding of fibrinogen to blood platelets and therefore are useful for inhibiting the aggregation of blood platelets.

European Patent Application 503,548 discloses cyclic urea derivatives (imidazolones and triazolones) useful in inhibiting cellular interactions and are therefore useful for treating or preventing, thrombosis, embolisms and metastases.

European Patent Application 496,378 discloses amidinobiphenyl compounds which inhibit cell-cell and cell-matrix interaction and are thus useful for treating thrombosis, cerebrovascular diseases, pulmonary embolisms, myocardial infarction, arteriosclerosis, osteoporosis and tumour metastases.

WO 93/09795 discloses non-peptide RGD analogs having terminal guanidino and carboxyl functions spaced by a chain of 11 atoms, at least 5 of which are carbon atoms, and containing no sequence of α-amino acids which compounds inhibit platelet aggregation and are useful for the treatment of several pathological disorders.

European Patent Application 445,796 discloses acetic acid derivatives which have inhibitory action on the bonding of adhesive proteins to blood platelets, as well as on blood platelet aggregation and cell-cell adhesion.

European Patent Application 372,486 discloses N-acyl beta amino acid derivatives and their salts. The disclosed compounds are useful for inhibiting platelet aggregation in the treatment of thrombosis, stroke, myocardial infarction, inflammation, arteriosclerosis, and for inhibiting metastasis.

European Patent Application 381,033 discloses amidino or guanidinoaryl substituted alkanoic acid derivatives useful for the treatment of thrombosis, apoplexy, cardiac infarction, inflammation, arteriosclerosis and tumors.

SUMMARY OF THE INVENTION

The present invention relates to a class of compounds represented by the formula:

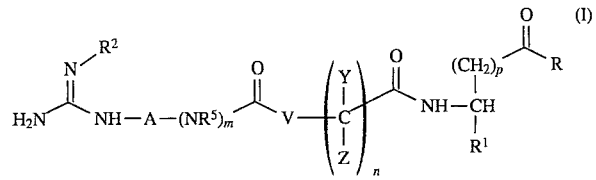

or a pharmaceutically acceptable salt thereof, wherein $R^2$ is selected from the group consisting of hydrogen, hydroxy, amino, alkoxy, lower alkyl and cyano;

A is selected from the group consisting of lower alkylene, lower alkenylene, and lower alkynylene which groups are optionally substituted by lower alkyl, lower alkenyl, lower alkynyl, cycloalkyl or aryl;

m is an integer 0 or 1;

$R^5$ is selected from the group consisting of hydrogen and lower alkyl;

V is selected from the group consisting of —CH$_2$—, —N(R$^6$)—, and monocyclic N-containing heterocycles, wherein $R^6$ is selected from the group consisting of H and lower alkyl;

Y and Z are independently selected from the group consisting of hydrogen, branched or straight lower alkyl and cycloalkyl;

n is an integer 0, 1, 2 or 3;

p is an integer 1, 2 or 3;

R is X—$R^3$ wherein X is selected from the group consisting of O, S and —NR$^4$, wherein $R^3$ and $R^4$ are independently selected from the group consisting of hydrogen, lower alkyl, aryl and arylalkyl; and $R^1$ is selected from the group consisting of alkyl, alkenyl, alkynyl, aryl, and monocyclic or bicyclic heterocycles wherein one to three carbon atoms are replaced by O, N or S.

It is another object of the invention to provide pharmaceutical compositions comprising compounds of the formula I. Such compounds and compositions have usefulness as modulators and/or inhibitors of platelet aggregation. The invention also relates to a method of therapeutically inhibiting or modulating platelet aggregation in a mammal in need of such treatment.

DETAILED DESCRIPTION OF THE INVENTION

The present invention relates to a class of compounds represented by the formula I, described above.

A preferred embodiment of the present invention is a compound of the formula I or a pharmaceutically acceptable salt thereof, wherein A is lower alkyl and m is 0. Most preferably, the compounds of the present invention are compounds wherein A is lower alkyl; m is 0; R is —OH or alkoxy and $R^1$ is pyridyl.

Embodiments exemplifying the present invention are the following compounds and pharmaceutically acceptable salts thereof:

methyl β-[[2-[[5-[(aminoiminomethyl)amino]-1-oxopentyl]amino]-1-oxoethyl]amino]3-pyridinepropanoate;

β-[[2-[[5-[(aminoiminomethyl)amino]-1-oxopentyl]amino]-1-oxoethyl]amino]3-pyridinepropanoic acid;

(±) ethyl β-[[2-[[4-[(aminoiminomethyl)amino]-1-oxobutyl]amino]-1-oxoethyl]amino]3-pyridinepropanoate;

(±) β-[[2-[[4-[(aminoiminomethyl)amino]-1-oxobutyl]amino]-1-oxoethyl]amino]3-pyridinepropanoic acid;

(±) ethyl β-[[2-[[6-[(aminoiminomethyl)amino]-1-oxohexyl]amino]-1-oxoethyl]amino]-3-pyridinepropanoate;

(±) β-[[2-[[6-[(aminoiminomethyl)amino]-1-oxohexyl]amino]-1-oxoethyl]amino]-3-pyridinepropanoic acid;

(±) β-[[3-[[4-[(aminoiminomethyl)amino]-1-oxobutyl]amino]-1-oxopropyl]amino]-3-pyridinepropanoic acid;

(±) ethyl β-[[2-[[4-[(aminoiminomethyl)amino]-1-oxo-3-phenylbutyl]amino]-1-oxoethyl]amino]-3-pyridinepropanoate;

(±) β-[[2-[[4-[(aminoiminomethyl)amino]-1-oxo-3-phenylbutyl]amino]-1-oxoethyl]amino]3-pyridinepropanoic acid;

ethyl βS-[[[1-[5-[(aminoiminomethyl)amino]1-oxopentyl]pyrrolidin-2-yl]carbonyl]amino-3-pyridinepropanoate;
and βS-[[[1-[5-[(aminoiminomethyl)amino]1-oxopentyl]pyrrolidin-2-yl]carbonyl]amino]-3-pyridinepropanoic acid.

As used herein, the terms "alkyl" or "lower alkyl" refer to a straight chain or branched chain hydrocarbon radicals having from about 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon-carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The terms "cycloalkyl" or "alicyclic hydrocarbon radical" as used herein mean a saturated or unsaturated cyclic carbon radical containing 3 to about 6 carbon atoms. Examples of such cycloalkyl radicals include cyclopropyl, cyclopropenyl, cyclobutyl, cyclopentyl, cyclohexyl, 2-cyclohexen-1-yl, and the like.

The terms "aryl," "arene," and "aromatic hydrocarbon radical" as used herein denote aromatic ring systems composed of one or more aromatic rings. Preferred aryl groups are those consisting of one, two or three aromatic rings. The term "aryl" embraces aromatic radicals such as phenyl, pyridyl, naphthyl, biphenyl and the like.

As used herein, the term "cyano" is represented by a radical of the formula

—CN.

The terms "hydroxy" and "hydroxyl" as used herein are synonomous and are represented by a radical of the formula

—OH.

As used herein the phrase "monocyclic or bicyclic heterocycle radicals" embraces monocyclic, or bicyclic radicals containing from 1 to 3 heteroatoms selected from the group consisting of oxygen, nitrogen and sulfur. Representative examples of heterocyclic radicals are furan, pyridine, benzofuran, pyran, thiophene, benzodioxole, benzothiophene and the like.

As used herein the term "monocyclic N-containing heterocycle" refers to monocyclic radicals containing from 3 to 7 atoms at least one of which is a nitrogen atom. Examples of such "monocyclic N-containing heterocycles" include piperidyl, piperizinyl, pyrrolidinyl and the like.

The symbol "BOC" as used herein refers to t-butoxycarbonyl.

The symbol "Δ" as used herein refers to heating the reaction mixture.

The abbreviation "DMF" as used herein means dimethylformamide.

The abbreviation "DIEA" as used herein refers to diisopropylethylamine.

The abbreviation "LiOH" as used herein refers to lithium hydroxide.

The abbreviation "TFA" as used herein refers to trifluoroacetic acid.

The term "lower alkylene" or "alkylene" as used herein refers to divalent linear or branched saturated hydrocarbon radicals of 1 to about 6 carbon atoms. The term "lower alkenylene" or "alkenylene" as used herein refers to divalent linear or branched hydrocarbon radicals containing at least one double bond and 2 to about 6 carbon atoms. As used herein the term "lower alkynylene" or "alkynylene" refers to divalent hydrocarbon radicals, linear or branched, containing one or more triple bonds and 2 to about 6 carbon atoms.

As used herein the term "alkoxy" refers to straight or branched chain oxy containing radicals of the formula —$OR_{10}$, wherein $R_{10}$ is an alkyl group as defined above. Examples of alkoxy groups encompassed include methoxy, ethoxy, n-propoxy, n-butoxy, isopropoxy, isobutoxy, sec-butoxy, t-butoxy and the like.

As used herein the term "arylalkyl" refers to a radical of the formula radical of the formula $R_{11}$—$R_{12}$—{ wherein $R_{11}$ is aryl wherein $R_{11}$ is aryl as defined above and $R_{12}$ is an alkylene as defined above.

The term "composition" as used herein means a product which results from the mixing or combining of more than one element or ingredient.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The compounds as shown in formula I can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of formula I with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of the pharmacologically acceptable salts may be prepared by conventional means. (See Berge et al., *J. Pharm. Sci.*, 66(1), 1–19 (1977) for additional examples of pharmaceutically acceptable salts.)

This invention also relates to a method of inhibiting platelet aggregation and more specifically, a method of treatment involving the administration of a therapeutically effective amount of a compound of the formula I together with pharmaceutically acceptable carrier to achieve such inhibition.

For the inhibition of platelet aggregation, compounds of the present invention may be administered orally, parenterally, or by inhalation spray, rectally, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the present invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus the dosage regimen may vary widely. Dosage levels of the order from about 0.01 mg to about 50 mg per kilogram of body weight per day are useful in the treatment of the above-indicated conditions.

For oral administration, the pharmaceutical composition may be in the form of, for example, a tablet, capsule, suspension or liquid. The pharmaceutical composition is preferably made in the form of a dosage unit containing a particular amount of the active ingredient. These may contain, for example, an amount of active ingredient from about 1 to 500 mg, preferably from about 25 to 350 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 10 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The compounds of formula I may be prepared by standard synthetic methods combined with methods analogous to solution phase peptide synthesis [see: *The Peptides: Analysis, Synthesis, Biology* (E. Gross and J. Meienhofer, eds.), Vol. 1–5, Academic Press, New York)].

The general synthetic sequences for preparing the compounds of the invention are outlined in Schemes I–VI.

SCHEME I

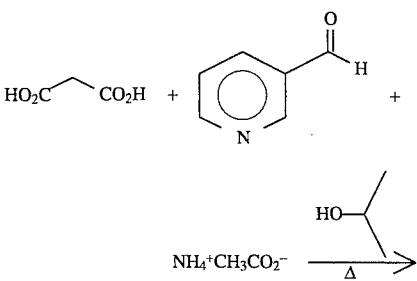

-continued
SCHEME I

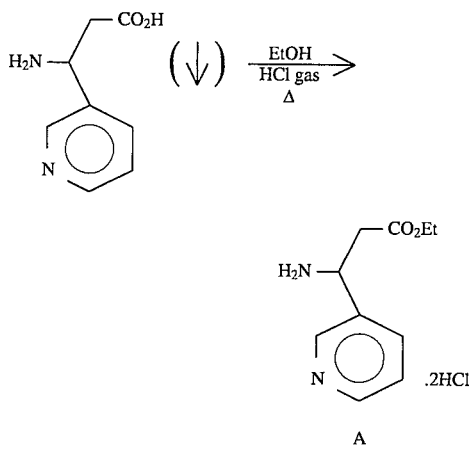

A

Scheme I describes a synthesis of a pyridyl β-aminoacid which can be used to synthesize compounds of the present invention wherein $R_1$ is pyridyl. The scheme can be modified using conventional methodology to prepare other aromatic, alkyl or heterocyclic substituted β-amino acids by substitution of the pyridyl carboxaldehyde with any other appropriate aldehyde. Briefly, in Scheme I to pyridinecarboxaldehyde in propanol is added ammonium acetate followed by malonic acid. The reaction mixture is stirred at reflux, the resulting precipitate filtered and washed with hot isopropanol and dried to yield 3-amino- 3-(3-pyridyl)propionic acid.

Additionally, β-Amino acids which are useful in the present invention are accessible through modified Knoevenagel reactions (Secor, H. V.; Edwards, W. B. J. *J. Org. Chem.* 1979, 44, 3136–40; Bellasoued, M.; Arous-Chtar, R.; Gaudemar, M. J.; *J. Organometal. Chem.* 1982, 231, 185–9), through Reformatski reaction with Schiff bases (Furukawa, M.; Okawara, T.; Noguchi, Y.; Terawaki, Y. *Chem. Pharm. Bull.* 1978, 26, 260), Michael addition into an acrylic derivative (Davies, S. G.; Ichihara, O. *Tetrahedron:Asymmetry* 1991, 2, 183–6; Furukawa, M.; Okawara, T.; Terawki, Y. *Chem. Pharm. Bull.*, 1977, 25, 1319–25). More recent methods include the use of organometallic reagents in Pd or Zn mediated couplings (Konopelski, J.; Chu, K. S.; Negrete, G. R. *J. Org. Chem.* 1991, 56, 1355; Mokhallalati, M. K.; Wu, M-J.; Prigden, L. N. *Tetrahedron Lett.* 1993, 34, 47–50) to complement more traditional reactions such as reductive amination of β-ketoesters.

The racemic beta-alkyl beta amino esters can also conveniently be prepared from the corresponding beta lactam by treatment with anhydrous HCl gas in ethanol. The beta lactams were prepared from the corresponding alkene and chlorosulfonyl isocyanate (Szabo, W. A. *Aldrichimica Acta*, 1977, 23). The latter method is useful for the preparation of α and β-substituted β-aminoacids. (Manhas, M. S.; Wagle, D. R.; Chong, J.; Bose, A. K. *Heterocycles*, 1988, 27, 1755.) Another route to α-substituted β-aminoacids is the Raney Nickel reduction of cyanoacetic esters at temperatures ranging between 20° and 80° C. and at 20 to 100 atm pressure (Testa, E.; Fontanella, L.; Fava, F. *Fermaco Ed. Sci.*, 1958, 13, 152; Testa, E.; Fontanella, L. *Annalen* 1959, 625, 95). Also, a number of procedures are available for the preparation of β-aminoacids by reduction of hydrazones of ketoacids (Gootijes, J.; Nomte, W. Th. *Rec. Trav. Chem.* 1953, 72, 721), oximes (Anziegin, A.; Gulewivich, W. *Z. Physiol. Chem.*, 1926, 158, 32) and nitropropionic acids. Purification of final compounds is usually by reverse phase high performance liquid chromatography (RP HPLC) [High Performance Liquid Chromatography Protein and Peptide Chemistry, F. Lottspeich, A. Henscher, K. P. Hupe, (eds.) Walter DeGruyter, New York, 1981] or crystallization.

SCHEME II

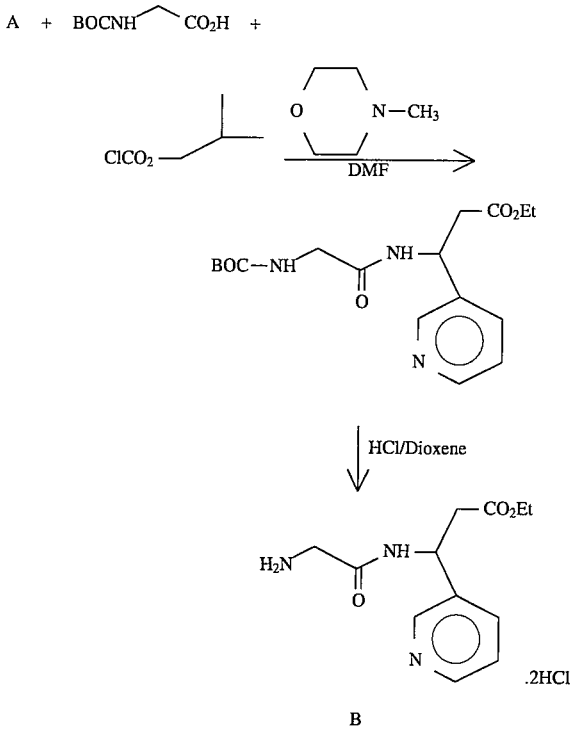

Scheme II is illustrative of methodology useful for coupling an α-amino acid to the β-amino acid compounds prepared in Scheme I. The compounds thus prepared are useful for coupling to guanidino-alkanoic and cycloalkanoic acid compounds to prepare the desired compounds of the present invention. Such methodology can be modified using conventional methodology to couple other aminoalkyl acids to the β-amino acids prepared in Scheme I.

Briefly, in Scheme II, to a solution of BOC-glycine in DMF is added 1-methyl morpholine followed by isobutylchloroformate. In a separate flask, the substituted β-amino acid in DMF is mixed with 1-methylmorpholine. The two mixtures are combined and stirred overnight to yield

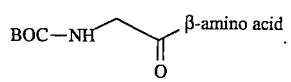

The resulting product is deprotected using HCl/Dioxane.

SCHEME III

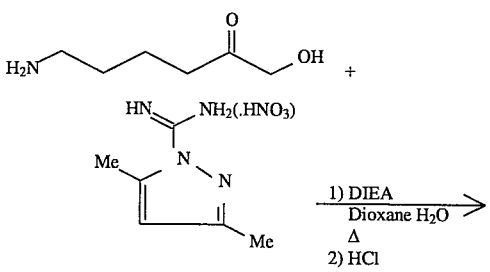

-continued
SCHEME III

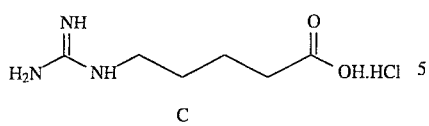

C

Scheme III is illustrative of methodology useful for preparing the guanidinoalkanoic acid or guanidinocycloalkanoic acid portion of the present invention which can be used for coupling to the β-amino acid. This can also be accomplished using other appropriate guanidating reagents known to those skilled in the art. The methodology of Scheme III can be modified using conventional techniques and methods to prepare alternate compounds useful for coupling to the β-amino acids.

Briefly, in Scheme III, to 3,5-dimethylpyrazole-1-carboxamidine nitrate in dioxane, water and DIEA, is added 5-aminovaleric acid. The mixture is stirred at reflux, the precipitate filtered, washed and dried. The precipitate is then further slurried in water, acidified and concentrated. The solvent is removed and the residue slurried and dried to yield 5-guanidinovaleric acid hydrochloride.

SCHMEME IV

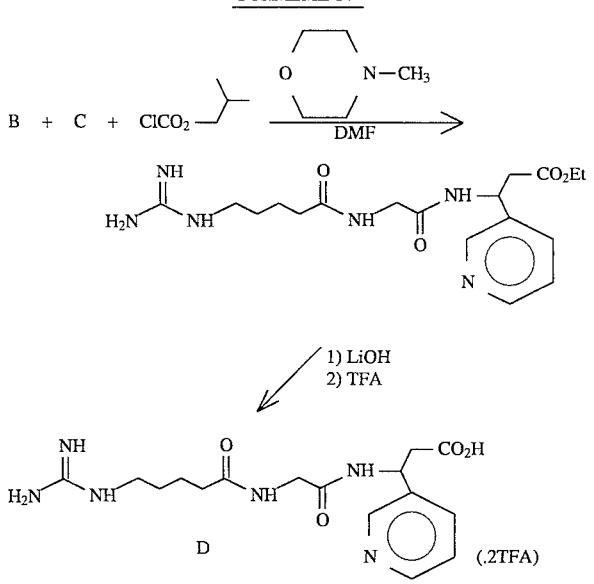

Scheme IV illustrates methodology useful for coupling the guanidino-alkyl acid to the β-amino acid portion of the desired compounds of the present invention. Such methodology can be modified using conventional methods known to those having ordinary skill in the art.

Briefly, in Scheme IV to the 5-guanidinovaleric acid (prepared in Scheme III) in DMF and N-methylmorpholine was added isobutylchloroformate. The reaction was stirred and a slurry of the β-amino acid compound (prepared in Scheme II) in DMF and N-methylmorpholine was added portionwise. The reaction was stirred, the precipitate filtered and washed with DMF. The DMF was removed. The resulting ester is dissolved in water, washed and LiOH is added to the aqueous layer and stirred. The solution is washed and treated with trifluoroacetic acid to pH=5. The solvent is removed and the product purified by RPHPLC to yield the desired compounds.

SCHEME V

Step A

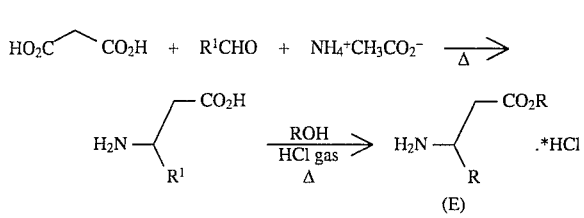

Step B

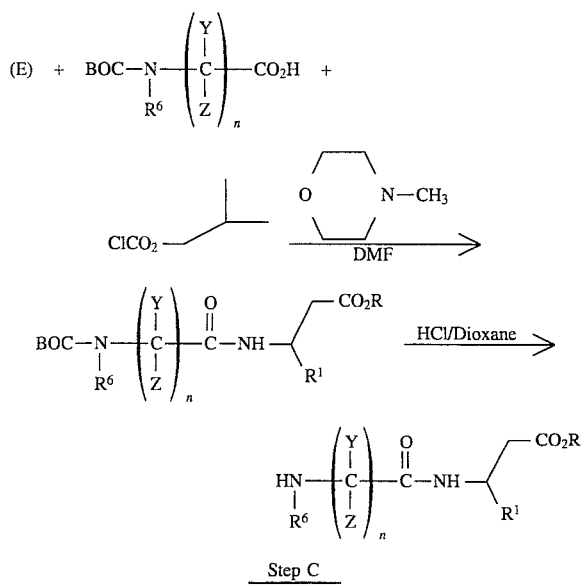

Step C

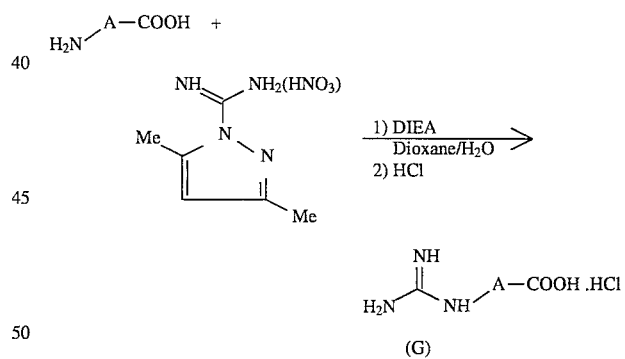

Step D

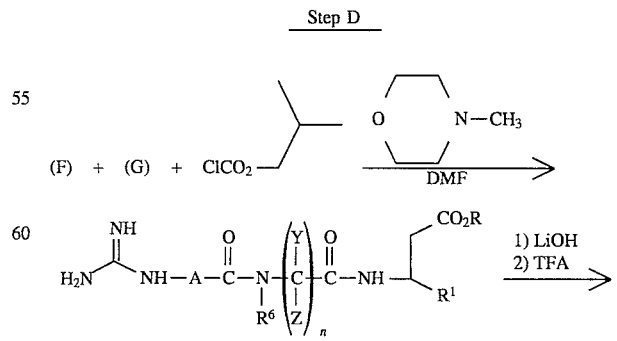

-continued
SCHEME V

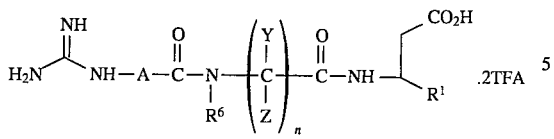

SCHEME VI

[for $(NR^5)_m$, where $m = 1$, $V = CH_2$]

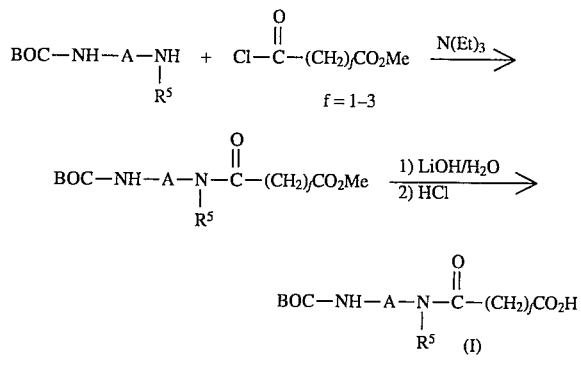

(I) + (E) (from Scheme V) +

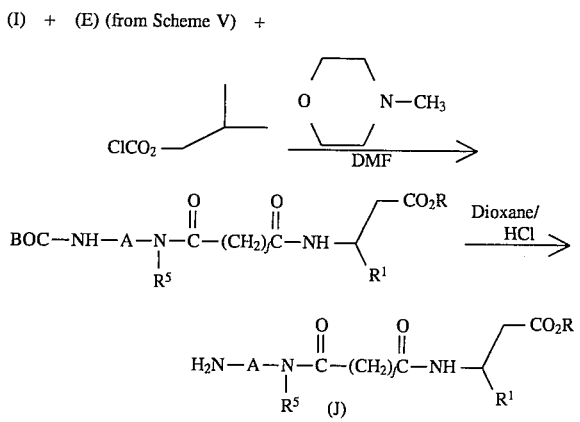

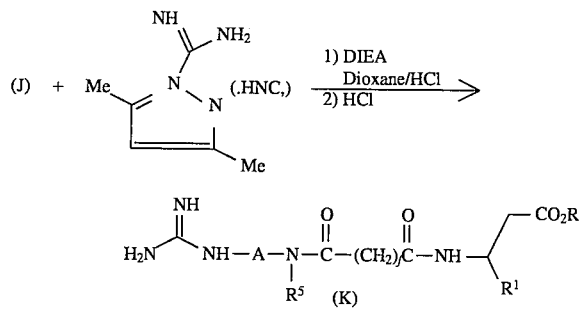

(K) + LiOH $\xrightarrow{TFA}$

-continued
SCHEME VI

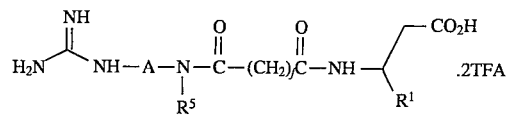

[For $(NR_5)_m$, where $m = 1$ and $V = N-R^6$ where $R^6 = H$ can be made as in Scheme VI but substituting $O=C=N-(CH_2)_fCO_2Me$ for
$Cl-\overset{O}{\overset{\|}{C}}(CH_2)f\,CO_2Me$ in the first Step.]

Schemes V and VI are illustrative of methodology useful for preparing various compounds of the present invention. Such methodology is more specifically defined in Schemes I–IV and the following Examples. Such methodology can be modified by one skilled in the art, substituting known reagents and conditions from conventional methodology to produce the desired compounds.

The following non-limiting examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

All the starting materials used in the examples are commercially available (or can be prepared by known methodology) as is all the equipment employed in the examples.

EXAMPLE 1

β[[2-[[5-[(aminoiminomethyl)amino]-1-oxopentyl]amino]-1-oxoethyl]amino]-3pyridinepropanoic acid, bistrifluoroacetate salt

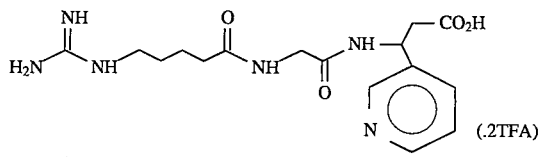

Step A

To 300 ml of 3-pyridine carboxaldehyde in 3 liters of 2-propanol was added 297 g of ammonium acetate followed by 398 g of malonic acid. The reaction mixture was stirred at reflux for 5 hours. The precipitate was filtered while hot and washed with 2 liters of hot isopropanol. The resulting white solid was then dried to yield 220 g of DL-3-amino-3-(3pyridyl)propionic acid as a white solid.

NMR and MS were consistent with the desired product.

Step B 220 g of DL-3-amino-3-(3-pyridyl)propionic acid from Step A was slurried in 3.6 liters of absolute EtOH. One lecture bottle (½ lb) of HCl gas was bubbled into the reaction while stirring over 40 minutes (slow exotherm to 61° C). The slurry was then heated at reflux for 4 hours (a solution forms after 1 to 1.5 hours). The reaction mixture was cooled to 5° C. in an ice bath. After stirring at 5° C. for 1.5 hours, the resulting white precipitate was filtered and washed thoroughly with ether. After drying under vacuum at 50° C., the yield of DL-ethyl-3-amino-3-(3-pyridyl)propionate dihydrochloride was 331.3 g as a white solid.

NMR and MS are consistent with the desired product.

Step C

To 220.6 g (0.83 mole) of DL-ethyl-3-amino-3-(3-pyridyl)-propionate dihydrochloride from Step B in 2 liters of anhydrous THF and 167.2 g (1.65 moles) of triethylamine, 225 g (0.826 moles) of N-t-BOC-glycine N-hydroxysuccinimide ester (Sigma) was added in several portions at 5°–10° C. (no exotherm). The reaction mixture was stirred overnight at room temperature. The resulting precipitate was filtered and washed with THF. The solvent from the filtrate was then removed under vacuum. The residue was taken up in 2.3 liters of ethyl acetate. The ethyl acetate layer was washed with saturated sodium bicarbonate (2×900 ml) and $H_2O$ (3×900 ml), dried over $MgSO_4$ and removed under vacuum. The residue was slurried overnight in 2.5 liters of 10% ethyl acetate/hexane. The precipitate was filtered, washed with 1 liter of 10% ethyl acetate/hexane, then hexane, then dried to yield 233 g of ethyl β-[[2-[[(1,1-dimethylethoxy)carbonyl]amino]-1-oxoethyl]amino]pyridine-3-propanoate as a white solid.

NMR and MS are consistent with the desired structure.

Step D 232 g (0.66 mole) of ethyl β-[[2-[[(1,1-dimethylethoxy)carbonyl]amino]-1-oxoethyl]amino]pyridine-3-propanoate (from Step C) was dissolved in 1 liter of warm dioxane. After cooling to room temperature, 1.6 liters of 4M HCl in dioxane (Aldrich) was slowly added. A white precipitate formed after several minutes and then turned to a thick goo. After 2 hours, the solvent was decanted off. Ether was slurried and decanted several times until a white solid resulted. This was dried under vacuum to yield 224.2 g of ethyl β-[(2-amino-1-oxoethyl]amino]pyridine-3-propanoate, bis(trifluoroacetate) salt as a white hygroscopic solid.

NMR and MS are consistent with the desired structure.

Step E

To 325 g (1.63 mole) of 3,5-dimethylpyrazole-1-carboxamidine nitrate (Aldrich) in 975 ml dioxane, 390 ml $H_2O$ and 283 ml (1.63 mole) diisopropylethylamine was added 121.6 g (1.04 mole) of 5-aminovaleric acid. This mixture was stirred at reflux for 1 hour and then at room temperature overnight. The precipitate was filtered, washed with 500 ml of dioxane and then washed with 1 liter of dioxane:$H_2O$ (1:1). The precipitate was air dried, then slurried in 500 ml $H_2O$ and acidified to pH=1 with concentrated HCl which resulted in a solution. The solvent was removed under vacuum and the residue slurried several times with ether (ether decanted off) and dried under vacuum to yield 179.8 g of 5-guanidino valeric acid hydrochloride as a white solid.

NMR and MS are consistent with the desired structure.

Step F

To 123.5 g (0.631 mole) of 5-guanidino valeric acid hydrochloride (from Step E) in 800 ml of anhydrous DMF (Aldrich) and 63.8 g (0.631 mole) of N-methyl morpholine was added dropwise over 10 minutes 88 g (0.631 mole) of isobutylchloroformate at 0°–5° C. (temperature kept below 15° C. during the addition with ice bath cooling). After stirring at ice bath temperature 5 additional minutes, a slurry was made up of 204.5 g (0.631 mole) ethyl β-[(2-amino-1-oxoethyl]amino]pyridine-3-propanoate, bis (trifluoroacetate) salt (in HCl)(from Step D) in 800 ml anhydrous DMF and 127.7 g (1.26 mole) N-methyl morpholine was added in several portions, keeping the reaction temperature below 20° C. with ice bath cooling. After addition was complete, the reaction was stirred overnight at room temperature. The precipitate was filtered off and washed with DMF. The DMF from the filtrate was removed under vacuum on a 75° C. water bath.

The residual ester was dissolved in 500 ml of warm $H_2O$. The $H_2O$ layer was washed 3 times with ethyl acetate and the ethyl acetate was discarded. To the aqueous layer was added 100 g of LiOH and this mixture was stirred at room temperature for 1.5 hours. The aqueous solution was washed 2 times with ether (ether discarded) and the aqueous layer was adjusted to pH=5 with trifluoroacetic acid. The solvent was removed under vacuum and the crude product was purified by reverse phase (C-18) preparative HPLC to yield 170 g of β-[[2-[[5-[(aminoiminomethyl)amino]-1-oxopentyl]amino]-1-oxoethyl]amino]-3-pyridinepropanoic acid, bistrifluoroacetate salt as a white solid.

NMR and MS are consistent with the desired structure.

EXAMPLE 2

βS-[[[1-[5-[(aminoiminomethyl)amino]-1-oxopentyl]pyrrolidin-2-yl]carbonyl]amino-3-pyridinepropanoic acid, bistrifluoroacetate salt

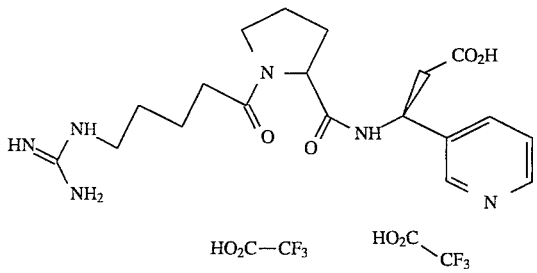

The above compound was prepared according to the method of Example 1 substituting 257.9 g of N-t-BOC-L-proline N-hydroxysuccinimide ester for N-t-BOC-glycine N-hydroxysuccinimide ester in Step C.

NMR and MS were consistent with the desired structure.

EXAMPLE 3

(±) β-[[2-[[4-[(aminoiminomethyl)amino]-1oxobutyl]amino]-1-oxoethyl]amino]-3pyridinepropanoic bistrifluoroacetate salt acid,

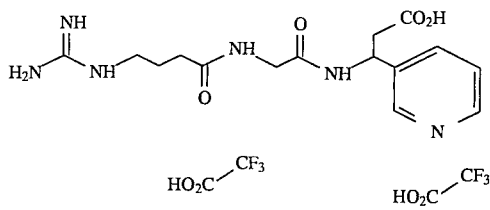

The above compound was prepared according to the methodology of Example 1 substituting 107.2 g of 4-aminobutanoic acid for the 5-aminovaleric acid in Step E.

NMR and MS are consistent with the desired structure.

EXAMPLE 4

(±) β[[2-[[6-[(aminoiminomethyl)amino]-1oxohexyl]amino]-1-oxoethyl]amino]-3-pyridinepropanoic acid, bistrifluoroacetate salt

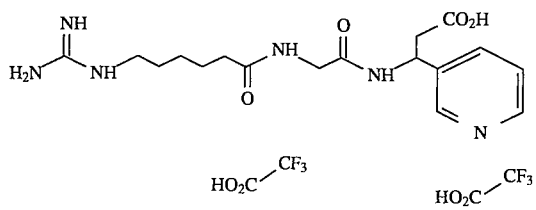

The above compound was prepared according to the methodology of Example 1 substituting 136.4 g of 6-aminohexanoic acid for the 5-aminovaleric acid in Step E.

NMR and MS are consistent with the desired structure.

EXAMPLE 5

(±) β-[[3-[[4-[(aminoiminomethyl)amino]-1-oxobutyl]amino]-1-oxopropyl]amino]-3-pyridinepropanoic acid, bistrifluoroacetate salt

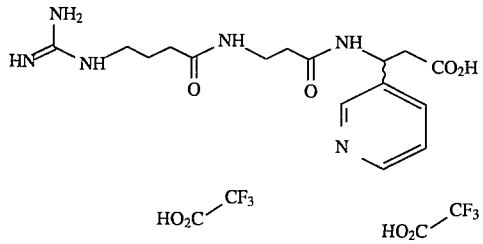

The above compound was prepared according to the method of Example 3 substituting 236.5 g of N-t-BOC-β-alanine-N-hydroxysuccinimide ester for N-t-BOC-glycine N-hydroxysuccinimide ester in Step C.

NMR and MS are consistent with the desired structure.

EXAMPLE 6

(±) β-[[2-[[4-[(aminoiminomethyl)amino]-1-oxo-3-phenylbutyl]amino]-1-oxoethyl]amino]-3-pyridinepropanoic acid, bistrifluoroacetate salt

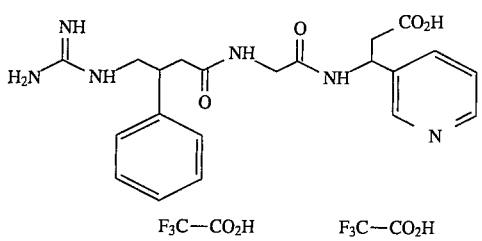

Step A 4-guinidino-3-p-chlorophenylbutyric acid hydrochloride was made using the method of Example 1 Step E, substituting 222.2 g of 4-amino-3-p-chlorophenylbutyric acid (RBI) for 5-aminovaleric acid. This product was reduced with 10% Pd/C in 50% EtOH/H$_2$O under 50 psi H$_2$ overnight to yield 4-guanidino-3phenylbutyric acid hydrochloride.

Step B

The title compound of Example 6 was made as in Example 1 Step F, substituting 162.6 g of the product of Example 6 Step A above for 5-guanidinovaleric acid hydrochloride.

NMR and MS are consistent with the desired structure.

PURIFIED IIb/IIIa RECEPTOR ASSAY

MATERIALS

Human fibrinogen receptor ($\alpha_{IIb}\beta_3$) was purified from outdated platelets. (Pytela, R., Pierschbacher, M. D., Argraves, S., Suzuki, S., and Rouslahti, E. "Arginine-Glycine-Aspartic acid adhesion receptors", *Methods in Enzymology* 144(1987):475–489.) Human vitronectin was purified from fresh frozen plasma as described in Yatohgo, T., Izumi, M., Kashiwagi, H., and Hayashi, M., "Novel purification of vitronectin from human plasma by heparin affinity chromatography," *Cell Structure and Function* 13(1988):281–292. Biotinylated human vitronectin was prepared by coupling NHS-biotin from Pierce Chemical Company (Rockford, Ill.) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", *J. Biol. Chem.* 266(3)(1991): 1415–1421.) Assay buffer, OPD substrate tablets, and RIA grade BSA were obtained from Sigma (St. Louis, Mo.). Anti-biotin antibody was obtained from Calbiochem (La Jolla, Calif.). GRGDSP peptide was purchased from Bachem (Torrance, Calif.). Linbro microtiter plates were obtained from Flow Labs (McLean, Va.). ADP reagent was obtained from Sigma (St. Louis, Mo.).

METHODS

Solid Phase Receptor Assays

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", Blood 70(1987):475–483. The purified human fibrinogen receptor ($\alpha_{IIb}\beta_3$) was diluted from stock solutions to 1.0 μg/mL in Tris-buffered saline containing 1.0 mM Ca$^{++}$, Mg$^{++}$, and Mn$^{++}$, pH 7.4 (TBS$^+$ ++). The diluted receptor was immediately transferred to Linbro microtiter plates at 100 μL/well (100 ng receptor/ well). The plates were sealed and incubated overnight at 4° C. to allow the receptor to bind to the wells. All remaining steps were at room temperature. The assay plates were emptied and 200 μL of 1% RIA grade BSA in TBS⁺⁺⁺(TBS⁺⁺⁺/BSA) were added to block exposed plastic surfaces. Following a 2 hour incubation, the assay plates were washed with TBS⁺⁺⁺ using a 96 well plate washer. Logarithmic serial dilution of the test compound and controls were made starting at a stock concentration of 2 mM and using 2 nM biotinylated vitronectin in TBS⁺⁺⁺/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was $1.0 \times 10^{-4}$M. The competition occurred for two hours after which all wells were washed with a plate washer as before. Affinity purified horseradish peroxidase labeled goat anti-biotin antibody was diluted 1:3000 in TBS⁺⁺⁺/BSA and 125 μL were added to each well. After 30 minutes, the plates were washed and incubated with ODD/$H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and % CV were determined for duplicate concentrations. The mean $A_{450}$ values were normalized to the mean of four maximum-binding controls (no competitor added)(B-MAX). The normalized values were subjected to a four parameter curve fit algorithm, (Robard, D., Munson, P. J., and de Lean, A., "Improved Curve Fitting, Parallelism/Testing, Characterization of Sensitivity and Specificity, Validation, and Optimization for Radioligand Assays" in *Radioimmunoassay and Related Procedures in Medicine*, Int. Atomic Energy Agency, Vienna, pp 469 (1977)), plotted on a semi-log scale, and the computed $IC_{50}$ and corresponding $R^2$ was reported. GRGDSP, a peptide fragment of fibrinogen was included on each plate as a positive control.

Human Platelet Rich Plasma Assays

Healthy aspirin free donors were randomly selected from a pool of volunteers. The harvesting of platelet rich plasma and subsequent ADP induced platelet aggregation assays were performed as described in Zucker, M. B., "Platelet Aggregation Measured by the Photometric Method", *Methods in Enzymology* 169(1989):117–133. Standard venipuncture techniques using a butterfly allowed the withdrawal of 45 mL of whole blood into a 60 mL syringe containing 5 mL of 3.8% trisodium citrate. Following thorough mixing in the syringe, the anti-coagulated whole blood was transferred to a 50 mL conical polyethylene tube. The blood was centrifuged at room temperature for 12 minutes at 200 × g to sediment non-platelet cells. Platelet rich plasma was removed to a polyethylene tube and stored at room temperature until used. Platelet poor plasma was obtained from a second centrifugation of the remaining blood at 2000 ×g for 15 minutes. Platelet counts are typically 300,000 to 500,000 per microliter. Platelet rich plasma (0.45 mL) was aliquoted into siliconized cuvettes and stirred (1100 rpm) at 37° C. for 1 minute prior to adding 50 uL of pre-diluted test compound. After 1 minute of mixing, aggregation was initiated by the addition of 50 uL of 200 uM ADP. Aggregation was recorded for 3 minutes in a Payton dual channel aggregometer (Payton Scientific, Buffalo, N.Y.). The percent inhibition of maximal response (saline control) for a series of test compound dilutions was used to determine a dose response curve. All compounds were tested in duplicate and half-maximal inhibition ($IC_{50}$) was calculated graphically from the dose response curve.

The assay results for the compounds of the present invention and their median inhibitory concentrations ($IC_{50}$) are recorded in Table I. The ester compounds of this invention are prodrugs of the acid compounds and thus when they are administered in vivo they are converted to the active acid compounds which are active as shown in Table I.

TABLE I

| Ex. # | R | IIb/IIIa/IC50(nm)* | Human Platelet Agg (uM)** |
|---|---|---|---|
| | H | 9.1 | 20 |
| 2 | H | 14.9 | ND |
| 3 | H | 3.13 | ND |
| 5 | H | 130 | 200 |
| 6 | | 28.9 | ND |
| 7 | H | 5.8 | ND |
| 5 | H | 49 | ND |
| 9 | H | 126 | ND |
| 10 | H | 14 | 30 |
| 8 | H | 400 | ND |

*Purified IIb/IIIa Receptor Assay
**ADP induced Aggregation of Human Platelet Rich Plasma
ND None detected

What is claimed is:

1. A compound of the formula

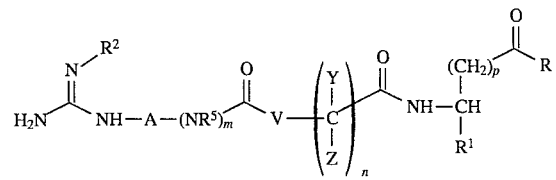

or a pharmaceutically acceptable salt thereof wherein $R^2$ is selected from the group consisting of hydrogen, and lower alkyl;

A is lower alkylene, optionally substituted by lower alkyl, cycloalkyl or aryl;

m is an integer 0 or 1;

$R^5$ is selected from the group consisting of hydrogen and lower alkyl;

V is selected from the group consisting of —$CH_2$—, and —N($R^6$)—, wherein $R^6$ is selected from the group consisting of H and lower alkyl;

Y and Z are independently selected from the group consisting of hydrogen, branched or straight lower alkyl and cycloalkyl;

n is an integer selected from 0, 1, 2 or 3;

p is an integer selected from 1, 2 or 3;

R is X-$R^3$ wherein X is selected from the group consisting of O, and S, wherein $R^3$ is selected from the group consisting of hydrogen, lower alkyl, aryl and arylalkyl; and $R^1$ is pyridyl.

2. A compound according to claim 1 wherein m is O and V is —N($R^6$).

3. A compound according to claim 2 or a pharmaceutically acceptable salt thereof selected from the group consisting of methyl β-[[2-[[5-[(aminoiminomethyl)amino]-1-oxopentyl]amino]-1-oxoethyl]amino]-3-pyridinepropanoate;

β-[[2-[[5-[(aminoiminomethyl)amino]-1oxopentyl] amino]-1-oxoethyl]amino]3-pyridinepropanoic acid;

(±) ethyl β-[[2-[[4-[(aminoiminomethyl)amino]-1-oxobutyl]amino]-1-oxoethyl]amino]3-pyridinepropanoate;

(±) β-[[2-[[4-[(aminoiminomethyl)amino]-1-oxobutyl]amino]-1-oxoethyl]amino]-3-pyridinepropanoic acid;

(±) ethyl β-[[2-[[6-[(aminoiminomethyl)amino]-1-oxohexyl]amino]-1-oxoethyl]amino]3-pyridinepropanoate;

(±) β-[[2-[[6-[(aminoiminomethyl)amino]-1-oxohexyl]amino]-1-oxoethyl]amino]3-pyridinepropanoic acid;

(±) β-[[3-[[4-[(aminoiminomethyl)amino]-1-oxobutyl]amino]-1-oxopropyl]amino]-3-pyridinepropanoic acid;

(±) ethyl β-[[2-[[4-[(aminoiminomethyl)amino]-1-oxo-3-phenylbutyl]amino]-1-oxoethyl-amino]-3-pyridinepropanoate;
and (±) β-[[2-[[4-[(aminoiminomethyl)amino]-1-oxo-3-phenylbutyl]amino]-1-oxoethyl-amino]-3-pyridinepropanoic acid.

4. A pharmaceutical composition comprising a therapeutically effective amount of a compound of the formula

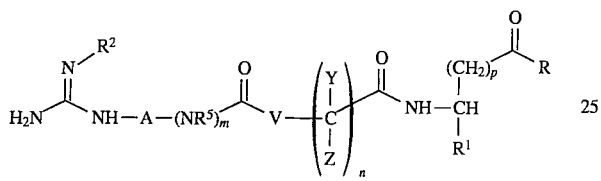

or a pharmaceutically acceptable salt thereof wherein $R^2$ is selected from the group consisting of hydrogen, and lower alkyl;

A is lower alkylene, optionally substituted by lower alkyl, cycloalkyl or aryl;

m is an integer 0 or 1;

$R^5$ is selected from the group consisting of hydrogen and lower alkyl;

V is selected from the group consisting of —$CH_2$—, and —$N(R^6)$—, wherein $R^6$ is selected from the group consisting of H and lower alkyl;

Y and Z are independently selected from the group consisting of hydrogen, branched or straight lower alkyl and cycloalkyl;

n is an integer selected from 0, 1, 2 or 3;

p is an integer selected from 1, 2 or 3;

R is $X-R^3$ wherein X is selected from the group consisting of O, and S wherein $R^3$ is selected from the group consisting of hydrogen, lower alkyl, aryl and arylalkyl;

$R^1$ is pyridyl; and
a pharmaceutically acceptable carrier.

5. A method of treating a mammal to inhibit platelet aggregation comprising administering a therapeutically effective amount of a compound of the formula

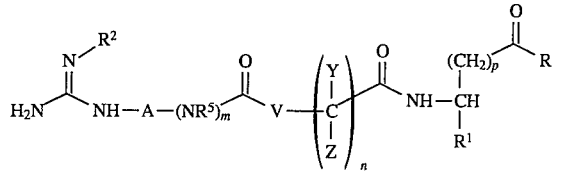

or a pharmaceutically acceptable salt thereof wherein $R^2$ is selected from the group consisting of hydrogen, and lower alkyl;

A is lower alkylene, optionally substituted by lower alkyl, cycloalkyl or aryl;

m is an integer 0 or 1;

$R^5$ is selected from the group consisting of hydrogen and lower alkyl;

V is selected from the group consisting of —$CH_2$—, and —$N(R^6)$—, wherein $R^6$ is selected from the group consisting of H and lower alkyl;

Y and Z are independently selected from the group consisting of hydrogen, branched or straight lower alkyl and cycloalkyl;

n is an integer selected from 0, 1, 2 or 3;

p is an integer selected from 1, 2 or 3;

R is $X-R^3$ wherein X is selected from the group consisting of O, and S wherein $R^3$ is selected from the group consisting of hydrogen, lower alkyl, aryl and arylalkyl; and $R^1$ is pyridyl.

6. A pharmaceutical composition according to claim 4 wherein the compound is selected from the group consisting of methyl β-[[2-[[5-[(aminoiminomethyl)amino]-1-oxopentyl]amino]-1-oxoethyl]amino]-3-pyridinepropanoate;

β-[[2-[[5-[(aminoiminomethyl)amino]-1-oxopentyl]amino]-1-oxoethyl]amino]-3-pyridinepropanoic acid;

(±) ethyl β-[[2-[[4-[(aminoiminomethyl)amino]-1-oxobutyl]amino]-1-oxoethyl]amino]-3-pyridinepropanoate;

(±) β-[[2-[[4-[(aminoiminomethyl)amino]-1-oxobutyl]amino]-1-oxoethyl]amino]-3-pyridinepropanoic acid;

(±) ethyl β-[[2-[[6-[(aminoiminomethyl)amino]-1-oxohexyl]amino]-1-oxoethyl]amino]-3-pyridinepropanoate;

(±) β-[[2-[[6-[(aminoiminomethyl)amino]-1-oxohexyl]amino]-1-oxoethyl]amino]-3-pyridinepropanoic acid;

(±) β-[[3-[[4-[(aminoiminomethyl)amino]-1-oxobutyl]amino]-1-oxopropyl]amino]-3-pyridinepropanoic acid;

(±) ethyl β-[[2-[[4-[(aminoiminomethyl)amino]-1-oxo-3-phenylbutyl]amino]-1-oxoethyl]-amino]-3-pyridinepropanoate;

(±) β-[[2-[[4-[(aminoiminomethyl)amino]-1-oxo-3-phenylbutyl]amino]-1-oxoethyl]-amino]-3-pyridinepropanoic acid.

7. A method according to claim 5 wherein the compound or a pharmaceutically acceptable salt thereof is selected from the group consisting of:

methyl β-[[2-[[5-[(aminoiminomethyl)amino]-1-oxopentyl]amino]-1-oxoethyl]amino]-3-pyridinepropanoate;

β-[[2-[[5-[(aminoiminomethyl)amino]-1-oxopentyl]amino]-1-oxoethyl]amino]3-pyridinepropanoic acid;

(±) ethyl β-[[2-[[4-[(aminoiminomethyl)amino]-1-oxobutyl]amino]-1-oxoethyl]amino]-3-pyridinepropanoate;

(±) β-[[2-[[4-[(aminoiminomethyl)amino]- 1-oxobutyl]amino]-1-oxoethyl]amino]-3-pyridinepropanoic acid;

(±) ethyl β-[[2-[[6-[(aminoiminomethyl)amino]-1-oxohexyl]amino]-1-oxoethyl]amino]-3-pyridinepropanoate;

(±) β-[[2-[[6-[(aminoiminomethyl)amino]-1-oxohexyl]amino]-1-oxoethyl]amino]-3-pyridinepropanoic acid;

(±) β-[[3-[[4-[(aminoiminomethyl)amino]-1-oxobutyl]amino]-1-oxopropyl]amino]-3-pyridinepropanoic acid;

(±) ethyl β-[[2-[[4-[(aminoiminomethyl)amino]-1-oxo-3-phenylbutyl]amino]-1-oxoethyl]-amino]-3-pyridinepropanoate; and (±) β-[[2-[[4-[(aminoiminomethyl)amino]-1-oxo-3-phenylbutyl]amino]-1-oxoethyl]-amino]-3-pyridinepropanoic acid.

\* \* \* \* \*